(12) United States Patent
Belson

(10) Patent No.: US 10,016,267 B2
(45) Date of Patent: *Jul. 10, 2018

(54) EMBOLIC PROTECTION DEVICE

(71) Applicant: Emboline, Inc., Los Altos, CA (US)

(72) Inventor: Amir Belson, Los Altos, CA (US)

(73) Assignee: Emboline, Inc., Santa Cruz, CA (US)

( * ) Notice: Subject to any disclaimer, the term of this patent is extended or adjusted under 35 U.S.C. 154(b) by 117 days.

This patent is subject to a terminal disclaimer.

(21) Appl. No.: 14/175,042

(22) Filed: Feb. 7, 2014

(65) Prior Publication Data

US 2014/0155929 A1 Jun. 5, 2014

Related U.S. Application Data

(63) Continuation of application No. 13/648,992, filed on Oct. 10, 2012, now Pat. No. 8,728,114, which is a continuation of application No. 13/347,046, filed on Jan. 10, 2012, now Pat. No. 8,308,754, which is a continuation of application No. 10/493,854, filed as
(Continued)

(51) Int. Cl.
*A61M 29/00* (2006.01)
*A61F 2/01* (2006.01)

(52) U.S. Cl.
CPC ............... *A61F 2/013* (2013.01); *A61F 2/01* (2013.01); *A61F 2002/018* (2013.01); *A61F 2230/0006* (2013.01); *A61F 2230/0069* (2013.01)

(58) Field of Classification Search
CPC ........ A61F 2002/018; A61F 2230/0006; A61F 2230/0069; A61F 2/01; A61F 2/013; A61F 2230/0017
See application file for complete search history.

(56) References Cited

U.S. PATENT DOCUMENTS

| 4,723,549 A | 2/1988 | Wholey et al. |
| 4,790,809 A | 12/1988 | Kuntz |

(Continued)

FOREIGN PATENT DOCUMENTS

| CA | 2609800 A1 | 1/2007 |
| WO | WO-03043538 A2 | 5/2003 |

(Continued)

OTHER PUBLICATIONS

US 6,348,062, 02/2002, Hopkins et al. (withdrawn)
(Continued)

*Primary Examiner* — Gregory Anderson
(74) *Attorney, Agent, or Firm* — Wilson Sonsini Goodrich & Rosati

(57) ABSTRACT

The embolic protection device (10) has an expandable tubular structure supporting a filter mesh material (12). The embolic protection device is compressed to a small diameter for insertion into a patient's aorta, then expanded within the aorta with the filter mesh material positioned to allow blood to enter sidebranch vessels connected to the aorta and to prevent embolic material from entering the sidebranch vessels. The filter mesh material may be configured with waves or undulations (26) for increased surface area and/or with two layers of mesh material to provide additional protection against embolization and to prevent inadvertent occlusion of the sidebranch vessels.

20 Claims, 5 Drawing Sheets

Related U.S. Application Data application No. PCT/US03/26938 on Aug. 27, 2003, now Pat. No. 8,114,114.

(60) Provisional application No. 60/406,492, filed on Aug. 27, 2002.

(56) References Cited

U.S. PATENT DOCUMENTS

| | | | |
|---|---|---|---|
| 5,108,419 | A | 4/1992 | Reger et al. |
| 5,197,485 | A | 3/1993 | Grooters |
| 5,769,816 | A | 6/1998 | Barbut et al. |
| 5,769,819 | A | 6/1998 | Schwab et al. |
| 5,797,880 | A | 8/1998 | Erskine |
| 5,800,525 | A | 9/1998 | Bachinski et al. |
| 6,013,051 | A | 1/2000 | Nelson |
| 6,117,154 | A | 9/2000 | Barbut et al. |
| 6,139,517 | A | 10/2000 | Macoviak et al. |
| 6,152,144 | A | 11/2000 | Lesh et al. |
| 6,254,563 | B1 | 7/2001 | Macoviak et al. |
| 6,258,120 | B1 | 7/2001 | McKenzie et al. |
| 6,348,063 | B1 | 2/2002 | Yassour et al. |
| 6,355,051 | B1 | 3/2002 | Sisskind et al. |
| 6,361,545 | B1 | 3/2002 | Macoviak et al. |
| 6,371,935 | B1 | 4/2002 | Macoviak et al. |
| 6,461,370 | B1 | 10/2002 | Gray et al. |
| 6,499,487 | B1 | 12/2002 | McKenzie et al. |
| 6,537,297 | B2 | 3/2003 | Tsugita et al. |
| 6,682,543 | B2 | 1/2004 | Barbut et al. |
| 6,695,864 | B2 | 2/2004 | Macoviak et al. |
| 6,746,469 | B2 | 6/2004 | Mouw |
| 6,808,520 | B1 | 10/2004 | Fourkas et al. |
| 7,232,453 | B2 | 6/2007 | Shimon |
| 7,235,060 | B2 | 6/2007 | Kraus |
| 7,758,606 | B2 | 7/2010 | Streeter et al. |
| 7,766,932 | B2 | 8/2010 | Melzer et al. |
| 8,114,114 | B2 | 2/2012 | Belson |
| 8,308,754 | B2 | 11/2012 | Belson |
| 8,414,482 | B2 | 4/2013 | Belson |
| 8,430,904 | B2 | 4/2013 | Belson |
| 8,679,149 | B2 | 3/2014 | Belson |
| 8,728,114 | B2 | 5/2014 | Belson |
| 9,107,734 | B2 | 8/2015 | Belson |
| 2001/0044632 | A1 | 11/2001 | Daniel et al. |
| 2002/0004667 | A1 | 1/2002 | Adams et al. |
| 2002/0045916 | A1* | 4/2002 | Gray .................... A61F 2/01 606/200 |
| 2002/0058964 | A1 | 5/2002 | Addis |
| 2002/0128680 | A1 | 9/2002 | Pavlovic |
| 2003/0040736 | A1 | 2/2003 | Stevens et al. |
| 2003/0100940 | A1 | 5/2003 | Yodfat |
| 2003/0171803 | A1 | 9/2003 | Shimon |
| 2004/0034380 | A1 | 2/2004 | Woolfson et al. |
| 2004/0073253 | A1 | 4/2004 | Morrill et al. |
| 2004/0138692 | A1 | 7/2004 | Phung et al. |
| 2004/0215167 | A1 | 10/2004 | Belson |
| 2004/0225354 | A1 | 11/2004 | Allen et al. |
| 2005/0010246 | A1 | 1/2005 | Streeter et al. |
| 2005/0283186 | A1 | 12/2005 | Berrada et al. |
| 2006/0287668 | A1 | 12/2006 | Fawzi et al. |
| 2006/0293706 | A1 | 12/2006 | Shimon |
| 2007/0027534 | A1 | 2/2007 | Bergheim et al. |
| 2007/0060944 | A1 | 3/2007 | Boldenow et al. |
| 2007/0073246 | A1 | 3/2007 | Simon |
| 2008/0027481 | A1 | 1/2008 | Gilson et al. |
| 2009/0149881 | A1 | 6/2009 | Vale et al. |
| 2010/0274277 | A1 | 10/2010 | Eaton |
| 2010/0312268 | A1 | 12/2010 | Belson |
| 2012/0016408 | A1 | 1/2012 | Barbut et al. |
| 2012/0109182 | A1 | 5/2012 | Belson |
| 2012/0109183 | A1 | 5/2012 | Belson |
| 2013/0035716 | A1 | 2/2013 | Belson |
| 2013/0035717 | A1 | 2/2013 | Belson |
| 2013/0096606 | A1 | 4/2013 | Bruchman et al. |
| 2013/0178891 | A1 | 7/2013 | Russell et al. |
| 2013/0238011 | A1 | 9/2013 | Belson |
| 2013/0245669 | A1 | 9/2013 | Basu et al. |
| 2014/0058372 | A1 | 2/2014 | Belson |
| 2014/0249568 | A1 | 9/2014 | Adams et al. |
| 2015/0066075 | A1 | 3/2015 | Russell et al. |
| 2015/0320540 | A1 | 11/2015 | Belson |
| 2017/0216010 | A1 | 8/2017 | Belson |
| 2017/0216011 | A1 | 8/2017 | Belson |

FOREIGN PATENT DOCUMENTS

| | | |
|---|---|---|
| WO | WO 2003/094791 A2 | 11/2003 |
| WO | WO 2004/019817 A1 | 3/2004 |

OTHER PUBLICATIONS

International search report and written opinion dated Apr. 9, 2008 for PCT/US2007/024558.
International search report and written opinion dated Apr. 22, 2013 for PCT Application No. US2013/20563.
International search report dated Jan. 15, 2004 for PCT/US2003/026938.
Notice of allowance dated Feb. 26, 2013 for U.S. Appl. No. 13/648,986.
Notice of allowance dated Mar. 1, 2013 for U.S. Appl. No. 13/343,538.
Notice of allowance dated Aug. 10, 2012 for U.S. Appl. No. 13/347,046.
Office action dated Jan. 17, 2012 for U.S. Appl. No. 12/532,630.
Office action dated Jan. 17, 2013 for U.S. Appl. No. 13/648,992.
Office action dated Jan. 24, 2014 for U.S. Appl. No. 13/735,864.
Office action dated Feb. 11, 2009 for U.S. Appl. No. 10/493,854.
Office action dated Feb. 26, 2008 for U.S. Appl. No. 10/493,854.
Office action dated Feb. 26, 2014 for U.S. Appl. No. 12/532,630.
Office action dated Mar. 13, 2013 for U.S. Appl. No. 12/532,630.
Office action dated Apr. 10, 2012 for U.S. Appl. No. 13/343,538.
Office action dated Apr. 10, 2013 for U.S. Appl. No. 12/532,630.
Office action dated Jun. 10, 2013 for U.S. Appl. No. 12/532,630.
Office action dated Jul. 12, 2011 for U.S. Appl. No. 10/493,854.
Office action dated Jul. 17, 2013 for U.S. Appl. No. 13/735,864.
Office action dated Jul. 23, 2013 for U.S. Appl. No. 13/648,992.
Office action dated Jul. 23, 2013 for U.S. Appl. No. 13/866,887.
Office action dated Aug. 20, 2010 for U.S. Appl. No. 10/493,854.
Office action dated Sep. 14, 2011 for U.S. Appl. No. 10/493,854.
Office action dated Nov. 6, 2012 for U.S. Appl. No. 12/532,630.
Office action dated Nov. 19, 2013 for U.S. Appl. No. 12/532,630.
Office action dated Dec. 11, 2012 for U.S. Appl. No. 13/343,538.
U.S. Appl. No. 14/537,814, filed Nov. 10, 2014, Russell et al.
Notice of Allowance dated Nov. 1, 2013 for U.S. Appl. No. 13/648,992.
Notice of Allowance dated Nov. 18, 2013 for U.S. Appl. No. 13/866,887.
Notice of Allowance dated Nov. 23, 2011 for U.S. Appl. No. 10/493,854.
International search report and written opinion dated Dec. 14, 2015 for PCT/US2015/049908.
Office action dated Nov. 6, 2015 for U.S. Appl. No. 14/801,850.
Co-pending U.S. Appl. No. 15/487,386, filed Apr. 13, 2017.
Co-pending U.S. Appl. No. 15/487,392, filed Apr. 13, 2017.

* cited by examiner

EMBOLIC PROTECTION DEVICE

CROSS-REFERENCE TO RELATED APPLICATION

This application is a continuation of U.S. patent application Ser. No. 13/648,992, filed Oct. 10, 2012, which is a continuation of U.S. patent application Ser. No. 13/347,046, filed Jan. 10, 2012, (now U.S. Pat. No. 8,308,754), which is a continuation of U.S. patent application Ser. No. 10/493,854, filed Apr. 27, 2004, (now U.S. Pat. No. 8,114,114), which is a National Stage Application of PCT/US2003/26938, filed Aug. 27, 2003, which claims the benefit of U.S. Provisional Application No. 60/406,492, filed Aug. 27, 2002, the full disclosures of which are incorporated herein by reference.

BACKGROUND OF THE INVENTION

1. Field of the Invention

The present invention relates to apparatus and methods for providing embolic protection to a patient's aortic arch vessels during cardiac surgery and interventional cardiology procedures.

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death. Prevention of cerebral embolism would benefit patients and improve the outcome of these procedures.

Previous devices for preventing cerebral embolism are described in the following U.S. patents and patent applications, which are hereby incorporated by reference: U.S. Pat. No. 6,371,935 Aortic catheter with flow divider and methods for preventing cerebral embolization, U.S. Pat. No. 6,361,545 Perfusion filter catheter, U.S. Pat. No. 6,254,563 Perfusion shunt apparatus and method, U.S. Pat. No. 6,139,517 Perfusion shunt apparatus and method, U.S. Pat. No. 6,537,297 Methods of protecting a patient from embolization during surgery, U.S. Pat. No. 6,499,487 Implantable cerebral protection device and methods of use, U.S. Pat. No. 5,769,816 Cannula with associated filter, US20030100940A1 Implantable intraluminal protector device and method of using same for stabilizing atheromas.

BRIEF SUMMARY OF THE INVENTION

The present invention takes the form of apparatus and methods for providing embolic protection to a patient's aortic arch vessels during cardiac surgery and interventional cardiology and electrophysiology procedures. Embolic particles in the aortic blood flow are prevented from entering the aortic arch vessels and carotid arteries that lead to the brain. The apparatus and methods of the present invention can also be used for embolic protection of other organ systems, such as the renal system.

In one embodiment, a stent-like embolic protection device is constructed of a self-expanding tubular mesh that may be woven out of wires or fibers or formed from a tube or sheet. The embolic protection device is compressed to a small diameter and inserted into a delivery tube or catheter, which is introduced via a peripheral artery or an aortotomy and advanced into the aortic arch. Once in place, the delivery tube is withdrawn to allow the device to expand similar to a self-expanding stent. The mesh of the device covers the ostia of the arch vessels, allowing blood to enter, but preventing potential emboli from entering the aortic arch vessels and carotid arteries. The device conforms closely to the walls of the aorta so that it will not interfere with performing cardiac surgery or interventional cardiology procedures. The embolic protection device may be collapsed and withdrawn from the aorta after the procedure or it may be left in the aorta for long-term embolic protection.

In another embodiment, the embolic protection device may be made with a flat panel of fine mesh textile fabric that is supported on a wire frame or the like. The panel of fine mesh fabric is held in place over the aortic arch vessels by the wire frame to filter out potential emboli. Being made of fabric, the device is free to conform to the ostia of the arch vessels to allow more surface area for blood flow compared to a flat panel. The wire frame may be attached to a handle or cannula for insertion through an aortotomy or to a catheter for peripheral artery insertion. In addition, the wire frame may include one or more wire hoops or a stent-like tubular structure for supporting the embolic protection device within the aortic arch.

Additional features are described which may be used with either embodiment of the embolic protection device. An embolic protection device is described with waves or undulations to provide more surface area for filtering out potential emboli and to prevent inadvertent occlusion of the arch vessels. Another embolic protection device is described with two layers of mesh material to provide additional protection against embolization and to prevent inadvertent occlusion of the arch vessels. An embolic protection device is described with an inflatable toroidal balloon for supporting the filter mesh material within the aorta. The embolic protection device or a portion of it may be coated with an antithrombogenic coating to reduce the formation of clots that could become potential emboli.

DETAILED DESCRIPTION OF THE INVENTION

Figure 1:
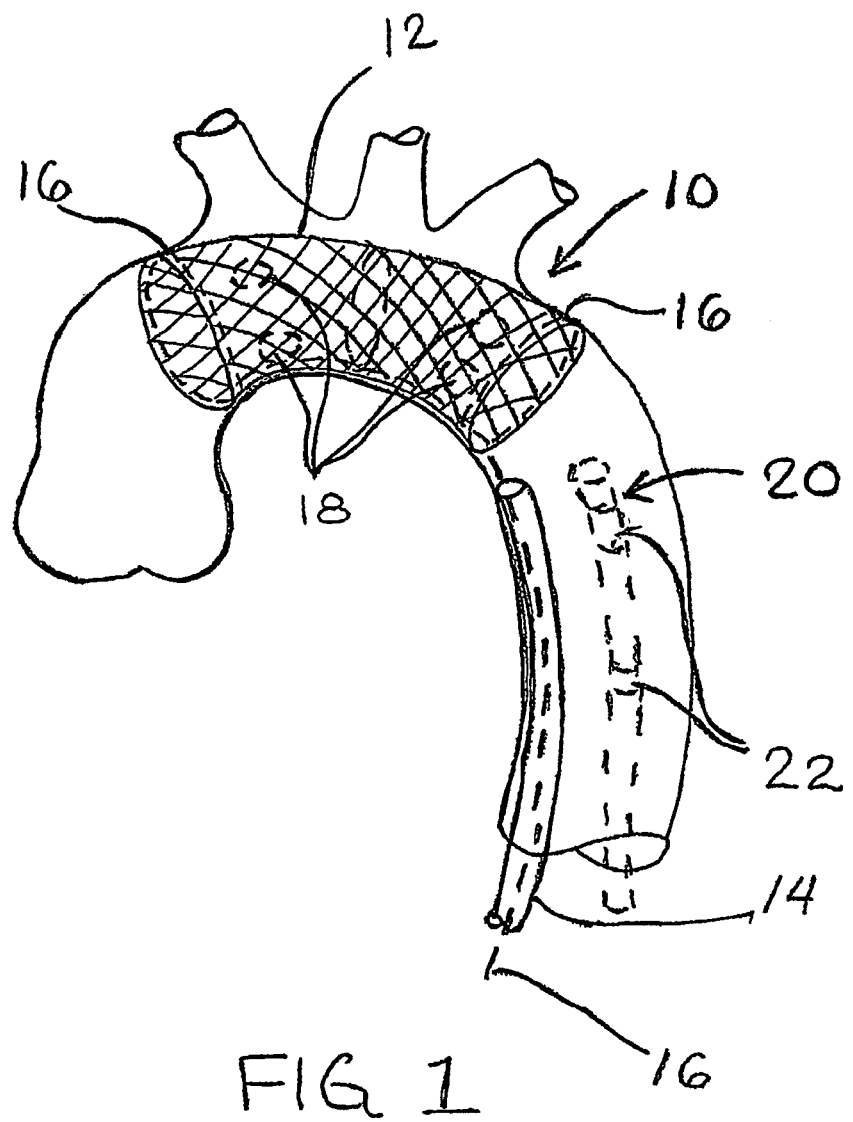
FIG. 1 shows a stent-like embolic protection device deployed within a patient's aortic arch for protecting the aortic arch vessels and carotid arteries from potential emboli.

FIG. 1 shows a stent-like embolic protection device 10 deployed within a patient's aortic arch for protecting the aortic arch vessels and carotid arteries from potential emboli. The embolic protection device 10 is made of a resilient material, either a polymer or a metal (e.g. Nitinol) or a combination of materials. The device 10 may be woven out of wires or fibers to form a tubular mesh structure 12 or by slitting and expanding a tube or sheet. Alternatively, the device 10 may be constructed with a tubular mesh structure 12 made of a flexible textile mesh with one or more wire hoops or a stent-like tubular structure for supporting the tubular mesh structure 12 within the aortic arch. The device 10 is compressible to a small diameter for insertion into the aorta via peripheral artery access or through an aortotomy. The device 10 is preferably self-expanding and, when expanded, has a generally tubular shape that conforms to the diameter and curvature of the aortic arch.

The embolic protection device 10 is compressed to a small diameter and inserted into a delivery tube or catheter 14. The delivery tube is introduced via a peripheral artery or an aortotomy and advanced into the aortic arch. Once in place, the delivery tube 14 is withdrawn to allow the device 10 to expand similar to a self-expanding stent. The mesh 12 of the device covers the ostia of the arch vessels, allowing blood to enter, but preventing potential emboli from entering the aortic arch vessels and carotid arteries. The device 10 conforms closely to the walls of the aorta so that it will not interfere with performing cardiac surgery or catheter-based interventional cardiology or electrophysiology procedures.

Alternatively, the embolic protection device 10 may be balloon-expandable. In this case, the embolic protection device 10 would be crimped or compressed onto an expandable balloon mounted on a catheter. The catheter is introduced into the aortic arch and the balloon is expanded to deploy the embolic protection device 10 in the aorta. Other volume expanding mechanisms, such as a mechanical expander, may be used in lieu of an expandable balloon.

After the procedure is completed, the embolic protection device 10 may be compressed and withdrawn from the aorta. Alternatively, the device 10 may be left in the aorta for long-term embolic protection. The device 10 may be compressed using one or more drawstrings 16 that encircle the device. The drawstrings 16 are pulled to compress the device and the device is withdrawn into the delivery tube 14 for removal. Alternatively, the embolic protection device 10 may be stretched longitudinal with the aid of a catheter, which will cause the diameter of the device to contract. Alternatively, the embolic protection device 10 may use a magnetic mechanism for compressing the device for removal. Multiple magnets 18 are arranged around the periphery of the device 10. After the procedure is completed, a catheter 20 carrying one or more strong magnets 22 is inserted through the lumen of the device 10 to compress the device around the catheter for removal.

Figure 2:
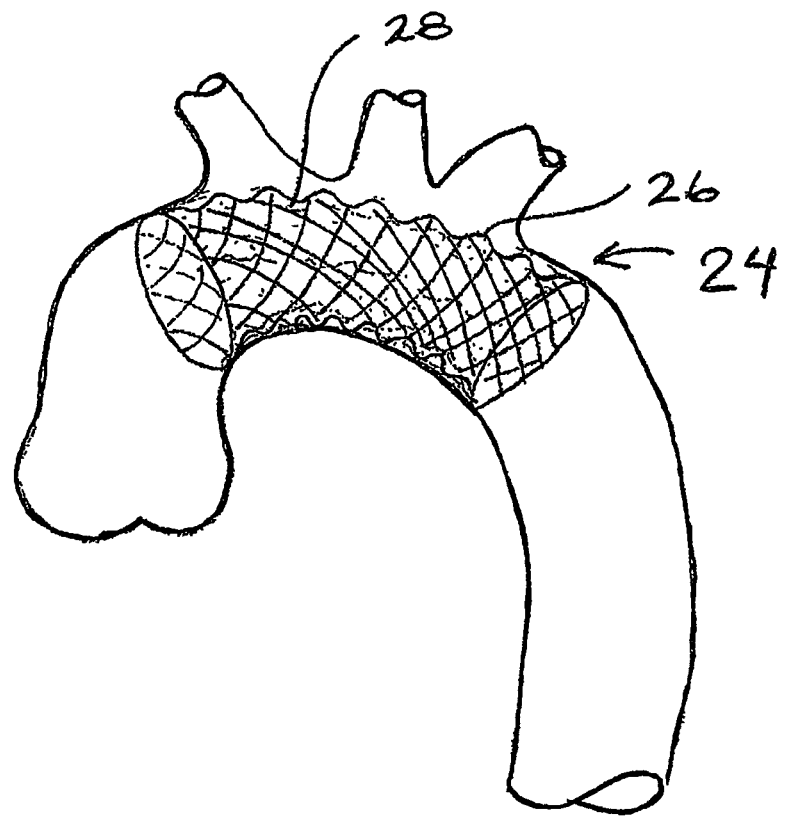
FIG. 2 shows a stent-like embolic protection device with waves or undulations.

FIG. 2 shows a stent-like embolic protection device 24 with waves or undulations 26 in the tubular mesh structure 28. The waves or undulations 26 in the embolic protection device 24 provide more surface area for filtering out potential emboli and prevents inadvertent occlusion of the arch vessels. This feature may be combined with any of the other embodiments and features of the invention described herein.

Figure 3:
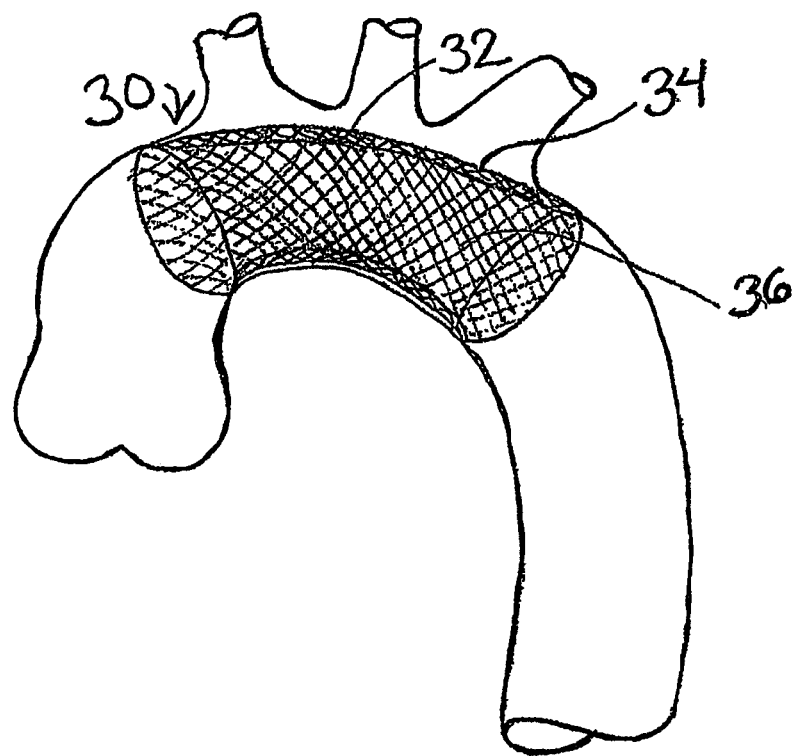
FIG. 3 shows a cut-away view of a stent-like embolic protection device with two layers of mesh material.

FIG. 3 shows a cut-away view of a stent-like embolic protection device 30 wherein the tubular mesh structure 32 is constructed with two layers of mesh material. The embolic protection device 30 preferably has an outer layer 34 of fine mesh material and an inner layer 36 of coarse mesh material. The outer layer 34 is shown cut away so that the inner layer 36 is visible. One or both layers of the device 30 may be self-expanding. For example, the outer layer 34 may be made of a fine mesh textile fabric, while the inner layer 36 is made with a self-expanding wire mesh structure. The two-layer structure provides additional protection against embolization and prevents the fine mesh of the outer layer 34 from becoming clogged with large emboli. Also, because blood can flow between the inner and outer layers of the device, all of the arch vessels will continue to receive blood flow even if the inner layer in front of one or more of the vessels becomes clogged. This feature may be combined with any of the other embodiments and features of the invention described herein. For example, one or both layers of the two-layer construction may be made with waves or undulations as described above in connection with FIG. 2. As illustrated in FIG. 3. the expandable structure may consist of the tubular mesh structure 32 which may consist of the outer layer 34 and the inner layer 36 free from external support, such as hoops and end rings, as illustrated in other embodiments herein.

Figure 4:
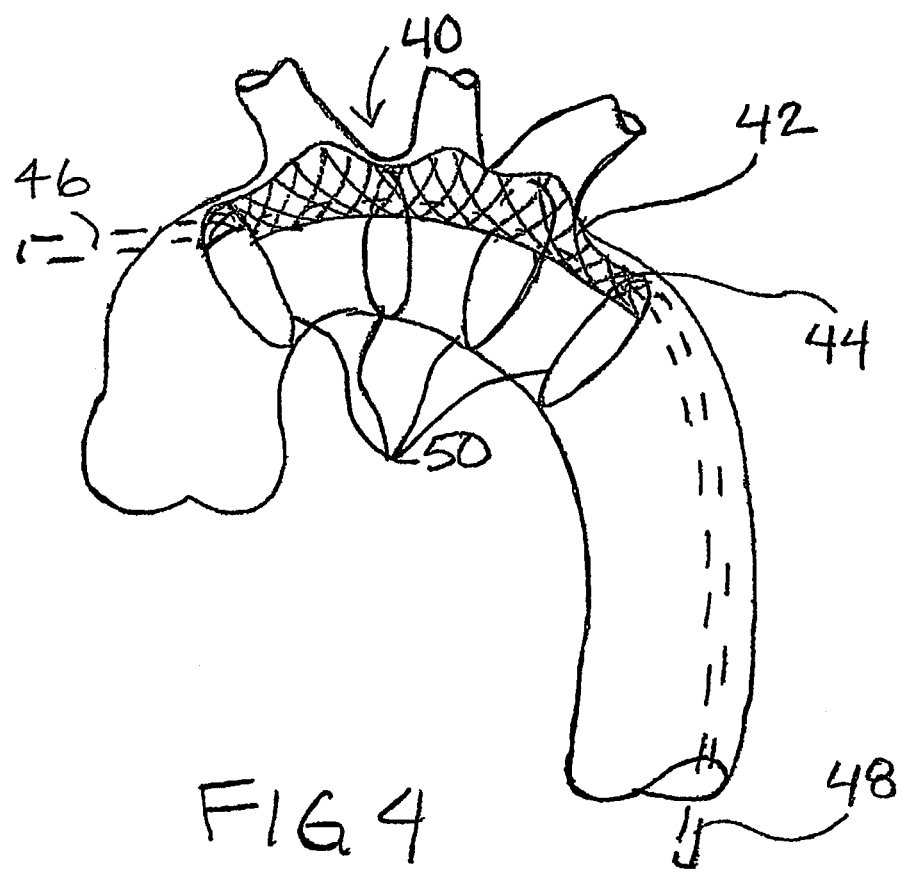
FIG. 4 shows an alternative embodiment of an embolic protection device.

FIG. 4 shows an alternative embodiment of an embolic protection device 40. In this embodiment, the embolic protection device 40 may be made with a panel of fine mesh textile fabric 42 that is supported on a wire frame 44 or the like. The panel of fine mesh fabric 42 is held in place over the aortic arch vessels by the wire frame 44 to filter out potential emboli. Being made of fabric, the mesh panel 42 is free to conform to the ostia of the arch vessels to allow more surface area for blood flow compared to a totally flat panel.

The wire frame 44 may be attached to a handle or cannula 46 for insertion through an aortotomy or to a catheter 48 for peripheral artery insertion. Alternatively or in addition, the wire frame 44 may include one or more wire hoops 50 or a stent-like tubular structure for supporting the embolic protection device 40 within the aortic arch. This embodiment and/or its features may be combined with any of the other embodiments and features of the invention described herein. For example, the mesh panel 42 may be made with waves or undulations as described above in connection with FIG. 2 and/or with a two-layer construction as described in connection with FIG. 3. As a further example, the handle, cannula 46 or catheter 48 for insertion of the embolic protection device 40 described in connection with FIG. 4 may also be combined with any of the embolic protection devices described in connection with FIGS. 1-3 and 5.

Figure 5:
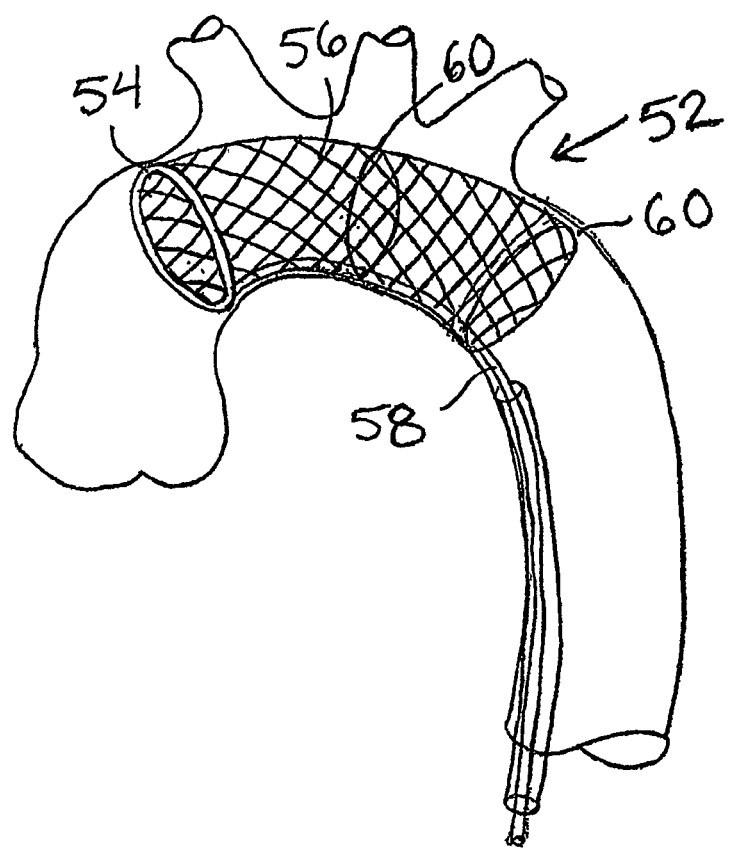
FIG. 5 shows another alternative embodiment of an embolic protection device.

FIG. 5 shows another alternative embodiment of an embolic protection device 52. An inflatable toroidal balloon 54 supports the upstream end of a tubular mesh structure 56. The toroidal balloon 54 is inflated and deflated through a catheter 58 having an inflation lumen and, optionally, a guidewire lumen. The tubular mesh structure 56 may be a self-expanding structure woven of wires or fibers or it may be a flexible textile mesh. Optionally, one or more wire hoops 60 or the like may be used to support the tubular mesh structure 56 within the patent's aorta. Alternatively, one or more additional inflatable toroidal balloons 54 may be used in place of the optional wire hoops 60 to support the tubular mesh structure 56. The features of this embodiment may be combined with any of the other embodiments and features of the invention described herein. For example, one or more inflatable toroidal balloons 54 may be combined with the embolic protection devices described in connection with FIGS. 1-3 for supporting a tubular mesh structure or panel of mesh material.

The entire embolic protection device or a portion of it may be coated with an antithrombogenic coating, for example a bonded heparin coating, to reduce the formation of clots that could become potential emboli. Alternatively or in addition, the embolic protection device or a portion of it may have a drug-eluting coating containing an anti-inflammatory or antistenosis agent.

The embolic protection device of the present invention can also be used for embolic protection of other organ systems. For example, an embolic protection device can be deployed in the patient's descending aorta for preventing embolic particles in the aortic blood flow from entering the renal arteries and embolizing in the patient's kidneys.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An embolic protection device for deployment within a patient's aorta comprising:
an expandable structure consisting of a tubular filter mesh material, the structure having a compressed configuration wherein the structure is compressed to a small width configured for insertion into the patient's aorta and an expanded configuration, wherein the filter mesh material is configured to expand to conform to or be held over the aortic vessels of the patient's aorta, wherein the filter mesh material consists of an inner layer of filter mesh and an outer layer of filter mesh, wherein the outer layer covers the inner layer, and wherein each of the inner layer and the outer layer comprises a self-expanding metal wire mesh structure, and wherein the filter mesh material is free from external support.

2. The embolic protection device of claim 1, wherein the inner layer of filter mesh comprises a coarse mesh material and the outer layer of filter mesh comprises a fine mesh material.

3. The embolic protection device of claim 1, wherein the inner layer and the outer layer are arranged so that blood can flow between the inner layer and the outer layer whereby the arch vessels will continue to receive blood flow even if the inner layer in front of one or more of the arch vessels becomes clogged.

4. The embolic protection device of claim 1, wherein the expandable structure is woven of resilient wires and/or fibers to form the filter mesh.

5. The embolic protection device of claim 1, wherein the filter mesh material is in a tubular configuration.

6. The embolic protection device of claim 1, wherein the filter mesh material is configured with waves or undulations.

7. The embolic protection device of claim 1, wherein at least a portion of the device is coated with an anti-thrombogenic coating.

8. The embolic protection device of claim 7, wherein the anti-thrombogenic coating comprises heparin.

9. The embolic protection device of claim 8, wherein the inner layer of filter mesh comprises a coarse mesh material and the outer layer of filter mesh comprises a fine mesh material.

10. The embolic protection device of claim 1, further comprising a delivery tube sized and configured to hold the expandable structure in its compressed position.

11. The embolic protection device of claim 1, wherein the tubular configuration is open at each end.

12. A method of providing embolic protection for sidebranch vessels connected to a patient's aorta comprising:
introducing an embolic protection device into the patient's aorta, the embolic protection device consisting of an expandable tubular structure consisting of filter mesh material, the structure having a compressed configuration wherein the structure is compressed to a small width for insertion into the patient's aorta and an expanded configuration, wherein the filter mesh material expands to conform to or be held over the aortic vessels of the patient's aorta such that the filter mesh material allows blood to enter the aortic vessels connected to the patient's aorta but prevents embolic material from entering the aortic vessels, wherein the filter mesh material is configured with an inner layer of filter mesh and an outer layer of filter mesh, wherein the outer layer covers the inner layer, and wherein each of the inner layer and the outer layer comprises a self-expanding metal wire mesh structure, and wherein the expandable tubular structure remains in place without external support.

13. The method of claim 12, wherein the inner layer of filter mesh comprises a coarse mesh material and the outer layer of filter mesh comprises a fine mesh material.

14. The embolic protection device of claim 12, wherein the inner layer and the outer layer are arranged so that blood can flow between the inner layer and the outer layer whereby the arch vessels will continue to receive blood flow even if the inner layer in front of one or more of the arch vessels becomes clogged.

15. The method of claim 12, wherein the expandable structure is woven of resilient wires and/or fibers to form the filter mesh.

16. The method of claim 12, wherein the filter mesh material is configured with waves or undulations.

17. The method of claim 12, wherein at least a portion of the device is coated with an anti-thrombogenic coating.

18. The method of claim 17, wherein the anti-thrombogenic coating comprises heparin.

19. The method of claim 12, wherein introducing comprises releasing the compressed embolic protection device from a delivery tube which holds the embolic protection device in its compressed position.

20. The method of claim 12, wherein the tubular configuration is open at each end.

* * * * *